United States Patent [19]

Jones

[11] Patent Number: 5,223,622

[45] Date of Patent: Jun. 29, 1993

[54] QUINAZOLIN-2-ONES

[75] Inventor: John D. Jones, Bury, Great Britain

[73] Assignee: Imperial Chemical Industries plc, London, England

[21] Appl. No.: 838,954

[22] Filed: Feb. 20, 1992

[30] Foreign Application Priority Data

Mar. 1, 1991 [GB] United Kingdom ............... 9104372

[51] Int. Cl.$^5$ ........................................... C07D 239/80
[52] U.S. Cl. ................................................... 544/286
[58] Field of Search ......................................... 544/286

[56] References Cited

FOREIGN PATENT DOCUMENTS 248554 12/1987 European Pat. Off. .
2503736 8/1978 Fed. Rep. of Germany .

OTHER PUBLICATIONS

Stefanovic, et al., Rec. Trav. Chim. Pays-bas; 80, 149 (1961).

*Primary Examiner*—John M. Ford
*Attorney, Agent, or Firm*—Joel G. Ackerman

[57] ABSTRACT

A process for preparing a compound of formula:

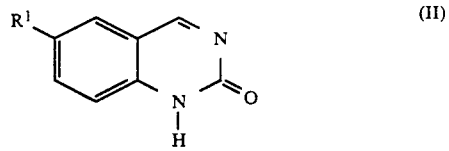

where $R^1$ is halogen, $CF_3$ or methyl; which process comprises decarboxylation of a compound of formula (III):

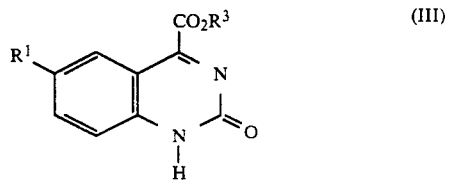

where $R^1$ is as defined above and $R^3$ is hydrogen or a cation.

Compounds of formula (III) and processes for their preparation are also claimed.

8 Claims, No Drawings

QUINAZOLIN-2-ONES

The present invention relates to novel 6-chloroquinazoline derivatives useful as intermediates in the preparation of herbicidal compounds, and to processes for preparing these intermediates.

The preparation of some 2-hydroxyquinazoline derivatives is described by G. J. Stefanovic et al in Recueil 1961, 80,149-157. European Published Patent Application No. 248554 describes certain quinazoline derivatives which are active as herbicides.

The compounds are prepared by various routes but a key intermediate used in the preparation of these compounds are compounds of formula (I): where $R^1$ is halogen, $CF_3$ or methyl and $R^2$ is a halogen group.

Compounds of formula (I) can be prepared by halogenation of a compound of formula (II): where $R^1$ is as defined in relation to formula (I).

Suitably halogenation is effected by reaction with a halogenating agent such as $POCl_3$ as described by Klaus Sasse in Synthesis 1978, (5) 379-82 or in EP-A-248554. Hitherto compounds of formula (II) have been prepared by cyclisation of a phenyl urea compound.

The applicants have found an alternative route to compounds of formula (II) involving the use of readily available starting materials and avoiding potentially yield-reducing by-product production.

According to the present invention there is provided a process for preparing a compound of formula (II) as hereinbefore defined, which process comprises decarboxylation of a compound of formula (III): where $R^1$ is as defined in relation to formula (I) and $R^3$ is hydrogen or a cation.

Examples of cations for $R^3$ include alkali metal and alkaline earth metal cations such as lithium, sodium, potassium or calcium. Suitably the cation is an alkali metal cation such as sodium or potassium preferably potassium.

Preferably $R^1$ is chlorine.

Decarboxylation where $R^3$ is hydrogen is effected simply by heating an aqueous solution of the compound of formula (III) to a temperature of from 50° to 100° C., preferably from 90° to 95° C. Where $R^3$ is a cation, this may first be acidified to convert $R^3$ to hydrogen by reaction with an inorganic acid such as hydrochloric acid at low temperatures suitably of from 0° C. to 10° C. preferably at about 5° C.

Preferably however the acidification and decarboxylation steps are carried out in a single step by heating the compound of formula (III) in the presence of dilute inorganic acid in particular dilute hydrochloric acid.

Compounds of formula (III) are novel compounds and as such form a part of the invention.

Compounds of formula (III) are prepared by reaction of a compound of formula (IV), where $R^1$ is as defined in relation to formula (I) and $R^4$ is a cation; with a compound of formula (V).

Suitable cations for $R^4$ are those described above in relation to $R^3$.

The reaction is suitable effected at elevated temperatures for example of from 100° C. to 150° C. suitably at about 130° C. Reaction can be achieved by melting the reactants together. Preferably however the reaction is effected in an appropriate organic solvent.

Azeotropic removal of water co-formed in the reaction is important if these elevated temperatures are to be maintained when the reaction is effected in an organic solvent. Hence the choice of solvent is important. Suitably the solvent is one which has at least some and preferably all of the following features:

i) it allows the reaction mass to remain stirrable and the product to be isolated by filtration;
ii) it forms an azeotrope with water;
iii) it allows the necessary reaction temperature to be achieved; and
iv) it is immiscible with water.

Examples of such solvents include pentan-1-ol, butan-1-ol, toluene and xylene.

Compounds of formula (IV) are suitably prepared by reaction of a compound of formula (VI), where $R^1$ is as defined in relation to formula (I) with a strong base.

Examples of suitable bases include alkali metal hydroxides, in particular potassium hydroxide.

The reaction is suitably effected at moderate temperatures, for example of from 0° C. to 40° C., preferably at temperatures of from 20° C. to 35° C., in the presence of an organic solvent such as pentan-1-ol. Preferably the solvent employed is the same as that used in the subsequent reaction of the compound of formula (IV) with the compound of formula (V). This allows the reaction to be carried out continuously without isolation of the compound of formula (IV).

Compounds of formula (V) and (VI) are known compounds or can be prepared from known compounds by conventional methods.

The following examples are given by way of illustration.

EXAMPLE 1

Step (1)

5-Chloroisatin (40 g, 89.45% w/w) was charged to a mixture of water (80 g) and pentan-1-ol (75 g) to produce a smooth slurry. The slurry was stirred at ambient temperature and potassium hydroxide pellets (14.41 g) added over 0.5 hours, maintaining the reaction temperature below 35° C. with water bath cooling. The colour changed from orange-brown to dark-brown, then purple, and finally, to yellow with a metallic lustre. Agitation of the reaction mixture, at about 35° C. was continued for 0.5 hours. More pentan-1-ol (250 g) was charged and the reaction mixture heated to reflux (96° C.) and the water azeotropically removed, using a Dean-Stark condenser, until the temperature of distillation reached 135° C. The mixture was cooled to 80° C. and urea (59.1 g) was charged in one portion. The reaction mixture was heated to reflux and water of reaction removed by azeotropic distillation over a period of about 4 hours. The yellow solid was filtered hot, reslurried and refluxed in methanol (400 g), to remove excess urea and condensed urea products, refiltered hot, washed with methanol (100 g), and dried at 70° C. to produce 4-potassium carboxylate-6-chloroquinazolin-2-one.

Elemental Analysis C, H, N, (Found) 40.5, 1.5, 10.6%. (Theory) 41.1, 1.5, 10.7%.

Step (2)

4-Potassium carboxylate-6-chloroquinazolin-2-one (45 g) from Step 1 was charged to water (225 g) and heated to 90° C. to produce a yellow slurry. A mixture of 36% hydrochloric acid (18 g) and water (7 g) was added over about 1.0 hour to the slurry at 90°-95° C. The mixture was stirred at 90°-95° C. for 0.5 hour, cooled to ambient temperature, filtered, washed with methanol, and dried at 70° C. to produce 6-chloroquinazolin-2-one.

Elemental Analysis: C, H, N (Found) 52.3, 3.1, 15.1%. (Theory) 53.2, 2.8, 15.5%.

CHEMICAL FORMULAE
(in description)

(I) [structure with $R^1$, $R^2$]

(II) [structure with $R^1$]

(III) [structure with $R^1$, $CO_2R^3$]

(IV) [structure with $R^1$, $C-CO_2R^4$, $NH_2$]

(V) $H_2NCNH_2$ (with C=O)

(VI) [isatin-type structure with $R^1$]

I claim:

1. A compound of formula (III)

(III) [structure with $R^1$, $CO_2R^3$]

in which $R^1$ is halogen, $CF_3$ or methyl and $R^3$ is hydrogen or a cation.

2. A compound according to claim 1 where $R^1$ is chloro.

3. A process for preparing a compound of formula (II)

(II) [structure with $R^1$]

where $R^1$ is halogen, $CF_3$ or methyl; which comprises
(a) reacting a compound of formula (IV)

(IV) [structure with $R^1$, $OR^4$, $NH_2$]

where $R^1$ is as defined above and $R^4$ is hydrogen or a cation; with a compound of formula (V)

(V) $H_2NCNH_2$ (with C=O)

in the presence of a solvent which forms an azeotrope with water but is immiscible with water to form a compound of formula (III);

(III) [structure with $R^1$, $CO_2R^3$]

in which $R^3$ is hydrogen or a cation; and
(b) decarboxylating the product of step (a) by heating to a temperature of from 50° to 100° C. in the presence of said solvent and water, under acidic conditions.

4. A process according to claim 3 in which step (a) is carried out at a temperature of from 100° C. to 150° C.

5. A process according to claim 3 in which the solvent is selected from pentan-1-ol, butan-1-ol, toluene and xylene.

6. A process according to claim 3 in which $R^4$ is hydrogen.

7. A process according to claim 3 in which $R^4$ is a cation, further comprising reacting a compound of formula (III) with an inorganic acid prior to, or in the same step as, step (b).

8. A process according to claim 3 in which step (b) is carried out by heating an aqueous acidic solution of the compound of formula (III).

* * * * *